US006933128B1

(12) United States Patent
Reddy et al.

(10) Patent No.: US 6,933,128 B1
(45) Date of Patent: Aug. 23, 2005

(54) CELL-BASED ASSAY FOR SCREENING COX-2 INHIBITORS

(75) Inventors: E. Premkumar Reddy, Villanova, PA (US); M. V. Ramana Reddy, Upper Darby, PA (US); Natarajan Dhanasekaran, Bryn Mawr, PA (US)

(73) Assignee: Temple University-of the Commonwealth System of Higher Education, Philadelphia, PA (US)

( * ) Notice: Subject to any disclaimer, the term of this patent is extended or adjusted under 35 U.S.C. 154(b) by 31 days.

(21) Appl. No.: 10/018,581

(22) PCT Filed: Jun. 15, 2000

(86) PCT No.: PCT/US00/16486

§ 371 (c)(1),
(2), (4) Date: Mar. 18, 2002

(87) PCT Pub. No.: WO00/77245

PCT Pub. Date: Dec. 21, 2000

Related U.S. Application Data

(60) Provisional application No. 60/139,569, filed on Jun. 16, 1999.

(51) Int. Cl.$^7$ ............................. C12N 9/00; C07H 21/04
(52) U.S. Cl. ................................. 435/25; 435/4; 435/6; 435/183; 435/189; 435/252.3; 435/320.1; 435/325; 536/23.2; 536/23.7; 514/789
(58) Field of Search .......................... 435/4, 6, 25, 183, 435/189, 195, 196, 252.3, 320.1, 325, 7.2, 7.31, 26, 28, 41, 91.1, 190, 192; 536/23.2–23.7; 514/789

(56) References Cited

FOREIGN PATENT DOCUMENTS

| AT | 402732 B | 8/1997 |
|----|----------|--------|
| AT | 402936 B | 9/1997 |
| WO | WO9414977 | 7/1994 |

OTHER PUBLICATIONS

Sheng et al. (J. Clinical Investigation, 1997, vol. 99(9):2254–2259).*
Dubois et al. (FASEB J., 1998, vol. 12:10631073).*
Laufer et al., Development of an in–vitro test system for the evaluation of cyclooxygenase–2 inhibitors, Inflamm. Res. Mar. 1, 1999, vol. 48, pp. 133–138, see entire document.
Brideau, et al., A human whole blood assay for clinical evaluation of biochemical efficacy of cyclooxygenase inhibitors, Inflamm. Res. Feb. 1, 1996, vol. 45, pp. 68–74, see entire document, especially p. 68, col. 2; p. 69, col. 2.

McCormack, K., Roles of COX–1 and COX–2, J. Rheumatol., Nov. 1, 1998, vol. 25, pp. 2279–2280, see entire document.
Xu, N. et al., A mutant $\alpha$ subunit of $G_{12}$ potentiates the eicosanoid pathway and is highly oncogenic in NIH 3T3 cells., Proc. Natl. Acad. Sci USA, Jul. 1, 1993, vol. 90, pp. 6741–6745, see entire document.
Dermott et al., Oncogenic mutant of $G\alpha_{12}$ stimulates cell proliferation through cycloxygenase–2 signaling pathway, Oncogene (1999) 18, 7185–7189.
Prasad et al., Activated mutant of $G\alpha_{13}$ induces EGR–1, c–fos, and transformation in NIH 3T3 cells, Oncogene (1994), 9, 2425–2429.
Zones et al., $G\alpha_{12}$ requires acylation for its transforming activity, Biochem. 1998, 37, 3196–3202.
Strathmann et al., $G\alpha 12$ and $G\alpha 13$ subunits define a fourth class of G protein $\alpha$ subunits, Proc. Natl. Acad. Sci. USA, vol. 88, pp. 5582–5586, Jul. 1991.
Kujubu et al., TIS10, a phorbol ester tumor promoter–inducible mRNA from Swiss 3T3 cells, encodes a novel prostaglandin synthase/cyclooxygenase homologue, The Journal of Biol. Chem., vol. 266, No. 20, Jul. 15, 1991, pp. 12866–12872.
Slice et al., $G\alpha_{13}$ stimulates rho–dependent activation of the cyclooxygenase–2 promoter, The Journal of Biol. Chem., vol. 274, No. 39, Sep. 24, 1999, pp. 27562–27566.
Dhanasekaran et al., Protein kinase C–dependent and –independent activation of Na+/H+ exchanger by $G\alpha_{12}$ class of G proteins, The Journal of Biol. Chem., vol. 269, No. 16, Apr. 22, 1994, pp. 11802–11806.
Prasad et al., Activation of Jun Kinase/Stress–activated protein kinase by GTPase–deficient mutants of $G\alpha_{12}$ and $G\alpha_{13}$, The Journal of Biol. Chem., vol. 270, No. 31, Aug. 4, 1995, pp. 18655–18659.

* cited by examiner

Primary Examiner—Manjunath N. Rao
(74) Attorney, Agent, or Firm—Drinker Biddle & Reath LLP (57) ABSTRACT

A cell-based assay is provided for screening substances for the capacity to inhibit COX-2 activity. The assay utilizes as a screening reagent a cell line which has been engineered to achieve constitutive or inducible expression of COX-2. In one embodiment, the cells express a GTPase-deficient, constitutively-activated mutant form of the $\alpha$-subunit of protein G12 which induces the production of arachidonic acid and COX-2. Decreased cell proliferation in the presence of test substance indicates that the substance has COX-2 inhibitory activity.

4 Claims, 7 Drawing Sheets

SEQUENCE LISTING

<160> NUMBER OF SEQ ID NOS: 4

<210> SEQ ID NO 1
<211> LENGTH: 18
<212> TYPE: DNA
<213> ORGANISM: Artificial Sequence
<220> FEATURE:
<223> OTHER INFORMATION: Mutagenic oligonucleotide for mutating the
      alpha subunit of protein G12

<400> SEQUENCE: 1
tgggcggcct gaggtcac                                                  18

<210> SEQ ID NO 2
<211> LENGTH: 18
<212> TYPE: DNA
<213> ORGANISM: Artificial Sequence
<220> FEATURE:
<223> OTHER INFORMATION: Mutagenic oligonucleotide for mutating the
      alpha subunit of protein G12

<400> SEQUENCE: 2
gtgacctcag gccgccca                                                  18

<210> SEQ ID NO 3
<211> LENGTH: 20
<212> TYPE: DNA
<213> ORGANISM: Artificial Sequence
<220> FEATURE:
<223> OTHER INFORMATION: Primer for cloning murine COX-2 DNA

<400> SEQUENCE: 3
ctctgcgatg ctcttccgag                                                20

<210> SEQ ID NO 4
<211> LENGTH: 23
<212> TYPE: DNA
<213> ORGANISM: Artificial Sequence
<220> FEATURE:
<223> OTHER INFORMATION: Primer for cloning murine COX-2 DNA

<400> SEQUENCE: 4
gacttttaca gctcagttga acg                                            23

CELL-BASED ASSAY FOR SCREENING COX-2 INHIBITORS

CROSS-REFERENCE TO RELATED APPLICATION

This is a 371 of PCT/US00/16486, filed Jun. 15, 2000 and published in English on Dec. 21, 2000 as International Publication No. WO 00/77245, which claims the benefit of the filing date of U.S. provisional patent application Ser. No. 60/139,569, filed Jun. 16, 1999, pursuant to 35 U.S.C. 119(e). The entire disclosure of the aforesaid provisional application is incorporated herein by reference.

REFERENCE TO GOVERNMENT GRANT

The invention described herein was supported in part by National Institutes of Health grant GM49897. The U.S. government has certain rights in the invention.

FIELD OF THE INVENTION

The invention relates to a method for the identification of compounds having biological activity. In particular, the invention relates to the identification of compounds which inhibit the activity of cycloxygenase-2.

BACKGROUND OF THE INVENTION

Heterotrimeric G Protein

Heterotrimeric guanine nucleotide-binding regulatory proteins ("heterotrimeric G proteins") that transduce signals from cell surface receptors to intracellular effectors are composed of $\alpha$, $\beta$ and $\gamma$ subunits. G$\alpha$ subunits are grouped based on amino acid homology into four subfamilies: $G_s$, $G_i$, $G_q$ and $G_{12}$ (Strathman and Simon, *Proc. Natl. Acad. Sci.* (*USA*) 1991; 88:5582–5582). The $\alpha$ subunits possess intrinsic GTPase activity and belong to a much larger group of GTPases which share structural elements. In all of these GTPases, a cycle of guanine nucleotide exchange and hydrolysis enables the protein to exist in two distinct states. The cycle allows G proteins to transiently relay signals from cell-surface receptors to intracellular effectors. Upon interaction with the appropriate agonist, the receptor serves to accelerate the exchange of GDP for GTP on the G protein $\alpha$ subunit. The exchange is believed to be accompanied by dissociation of the $\alpha$ and $\beta$-$\gamma$ subunits, allowing $\alpha$(and in some cases $\beta$-$\gamma$) to interact with effectors. The intrinsic GTPase activity terminates the signal, returning the $\alpha$ subunit to its basal GDP-bound state. Studies have suggested that the $G_{12}$ members $\alpha_{12}$ and $\alpha_{13}$ regulate signaling pathways involved in controlling cell growth and differentiation. See Vara Prasad et at, *J. Biol. Chem.* 1995, 270:18655–18659.

The full-length cDNAs encoding mouse G$\alpha$12 and G$\alpha$3, and the encoded translation products, are disclosed in Strathman and Simon, supra, the entire disclosure of which is incorporated herein by reference. The sequences have been deposited in the GenBank data base by the authors, accession nos. M63659 (G$\alpha$12) and M63660 (G$\alpha$13). Those GenBank records are incorporated herein by reference. The human G$\alpha_{12}$ cDNA has also been cloned (Chan et at., *Mol. Cell. Biol.* 1993; 13:762–768, incorporated herein by reference).

When constitutively activated, GTP-binding proteins can induce neoplastic transformation. See Xu et al., *Proc. Natl. Acad. Sci.* (*USA*) 1993: 90:6741–6745, the entire disclosure of which is incorporated herein by reference. Overexpression of wild-type G$\alpha_{12}$ in NIH 3T3 cells is weakly transforming; a GTPase-deficient mutant of G$\alpha_{12}$ (G$\alpha_{12}$Q229L) behaves as a potent oncogene and is highly transforming in NIH 3T3 cells (Xu et al., supra). It has been found that G$\alpha_2$-transfected cells exhibit a remarkably increased level of arachidonic acid in response to serum, and this effect is observed in cells transfected with either wild-type or activated mutant G$\alpha_{12}$ (Xu et al., supra).

The G$\alpha_{12}$Q229L mutant results from insertion of a leucine residue at position 229 in lieu of glutamine in the wild-type G$\alpha_{12}$ protein. The mutation occurs in a highly conserved region in G proteins which is involved in binding and GTPase activity. The Q229L mutation results in a GTPase-deficient form of G$\alpha_{12}$. The mutation blocks GTPase activity so that the $\alpha$ subunit binds GTP and is constitutively active (Xu et al., supra; Dhanasekaran et al., *J. Biol. Chem.* 1993, 269:11802–11806; Jian et al., FEBS Left. 1993; 330:319–322; Vara Prasad et al., *Oncogene* 1994, 9:2425–2429; Voyno-Yasenetskaya et al., *Oncogene* 1994; 9:2559–2565).

COX-2

Cyclooxygenase-1 (COX-1) and cyclooxygenase-2 (COX-2) are the enzymes which convert arachidonic acid into prostaglandins. COX-1 is ubiquitously expressed and involved in cellular "housekeeping" functions of various tissues and organs. In contrast, COX-2 expression is rapidly induced in diverse cell types by different growth factors, mitogens, tumor promoters, and physiological stress stimuli. Transcriptional induction of COX-2 has been shown to be involved in different pathological conditions such as inflammation, pain, and fever. It has also been shown that the anti-inflammatory effects of aspirin and ibuprofen is through their inhibitory effect, albeit non-specific inhibitory effect, on COX-2. Furthermore, persistent activation of COX-2 has been shown to be associated with oncogenesis as well as the invasive potential of tumor cells.

Inhibitors of COX-2 are useful as therapeutics. See, for example, the discussion of the advantages of selective COX-2 inhibition set forth in U.S. Pat. No. 5,604,253.

What is needed is a simple, sensitive and rapid screening method for determining the COX-2 inhibitory activity of therapeutic candidates.

SUMMARY OF THE INVENTION

It is an object of the invention to provide a screening method to determine the COX-2 inhibitory activity of chemical compounds.

It is an object of the invention to provide a screening method for COX-2 inhibition which relies on cells which respond to the presence of COX-2 inhibitor by reducing proliferation in comparison to cells of the same type which are not contacted with COX-2 inhibitor.

It is an object of the invention to provide a screening method for COX-2 inhibition which relies on cells which respond to the presence of COX-2 inhibitor by increasing production of one or more prostaglandins in comparison to cells of the same type which are not contacted with COX-2 inhibitor.

It is an object of the invention to provide a screening method for COX-2 inhibition which relies on cells which respond to the presence of COX-2 inhibitor by accumulating arachidonic acid in comparison to cells of the same type which are not contacted with COX-2 inhibitor.

A method for screening a test substance for COX-2 inhibitory activity is provided. The test substance is contacted with indicator cells which constitutively or inducibly express endogenous COX-2. The level of proliferation of the indicator cells is determined in the presence and absence of the test substance. A decreased level of proliferation of the indicator cells in the presence of the test substance indicates that the test substance has COX-2 inhibitory activity.

According to another method for screening a test substance for COX-2 inhibitory activity, the test substance is contacted with indicator cells which constitutively or inducibly express COX-2, and the level of one or more prostaglandins produced by the indicator cells is determined in the presence or absence of the test substance. A decreased level of one or more prostaglandins produced by the indicator cells in the presence of a test substance indicates that the test substance has COX-2 inhibitory activity.

According to another method for screening a test substance for COX-2 inhibitory activity, the test substance is contacted with indicator cells which constitutively or inducibly express COX-2, and the level of arachidonic acid provided by the indicator cells is determined in the presence or absence of the test substance. An increased level of arachidonic acid provided by the indicator cells in the presence of a test substance indicates that the test substance has COX-2 inhibitory activity.

According to preferred embodiments of the invention, indicator cells constitutively or inducibly express endogenous COX-2. According to other preferred embodiments of the invention, the indicator cells express a GTPase-deficient mutant form of the α-subunit of protein G12. The mutant α-subunit has the capacity to induce the production of arachidonic acid and COX-2 in the indicator cells.

According to one embodiment of the invention, the G12 protein α-subunit mutant comprises the Q229L mutation.

The level of indicator cell proliferation is conveniently determined by an assay for DNA synthesis by the indicator cells. According to one embodiment, the DNA synthesis assay comprises assaying tritium-labeled thymidine uptake by the indicator cells.

The level of indicator cell production of one or more prostaglandins is conveniently determined with resort to any assay which is capable of quantifying, at least in relative terms as compared to control cells, the level of production of such prostaglandins. According to a preferred embodiment, the prostaglandin assay method comprises an immunoassay. According to a more preferred embodiment, the immunoassay comprises a competitive immunoassay for a prostaglandin.

The level of arachidonic acid in the indicator cells, the components thereof, or released into the medium surrounding the cells, is conveniently determined with resort to any assay which is capable of quantifying, at least in relative terms as compared to control cells, the level of arachidonic acid. One such method is a radiolabeling assay. According to one embodiment, the assay comprises assaying release of tritiated arachidonic acid by the indicator cells.

DETAILED DESCRIPTION OF THE INVENTION

A cell based bioassay system is provided for screening compounds for COX-2 inhibitory activity by assaying the growth-inhibitory property of the compounds when exposed to COX-2 growth-driven target cells. The target cells are cells which are capable of growing in culture but which have been engineered to constitutively or inducibly express COX-2, preferably endogenous COX-2.

By "expression" with respect to COX-2 is meant the production of active COX-2 enzyme by the cell.

By "endogenous" with respect to COX-2 is meant DNA sequences corresponding to the native, COX-2 gene locus, its variants, or derivatives present in the cells of the organism from which a given indicator cell line was derived.

By "constitutively express" with respect to COX-2 is meant that biologically active COX-2 protein is present continually in a cell and does not appear to be subject to quantitative regulation.

By "inducibly express" with respect to COX-2 is meant that the COX-2 gene is activated in response to a specific stimulus, such as the presence of a specific small molecule inducer, to produce biologically active COX-2 protein. The gene is not activated, or activated only at a much lower level, in the absence of the specific stimulus. Inducible expression of the COX-2 gene may be controlled directly to achieve inducible expression, such as by an inducible promoter operably linked to a COX-2 gene in an expression construct. Alternatively, inducible expression of the COX-2 gene may be controlled indirectly, such as by an inducible promoter operably linked to a second gene other than the COX-2 gene. The inducible expression of the second gene in turn governs the expression of COX-2.

COX-2 is activated by several different pathways in the cell (Vane et al., *Annu. Rev. Pharmacol. Toxicol.* 1998; 38:97–120, incorporated herein by reference). Each pathway is a target for manipulation of COX-2 gene expression to achieve either constitutive or inducible expression of that gene. Cell lines which express endogenous COX-2 and produce prostaglandins may be appropriate indicator cells for screening for COX-2 inhibitors. An example of such a cell line is the MDA-MB-231 human breast cancer cell line (ATCC number HTB-26; Liu and Rose, *Cancer Res.* 110 1996; 56:5125–5127, incorporated herein by reference).

According to one embodiment, the indicator cells express a GTPase-deficient, constitutively-activated mutant form of the α-subunit of the heterotrimeric protein G12 ("$G\alpha_{12}$ mutant"). By "GTPase-deficient" is meant that the molecule lacks intrinsic GTPase activity. Hence, the $G\alpha_{12}$ mutant is constitutively active. By "constitutively activate" is meant that the activity of the protein is present essentially continually in the cell and is not subject to quantitative regulation. The $G\alpha_{12}$ mutant has the property of inducing the production of arachidonic acid. Arachidonic acid is a substrate of COX-2. COX-2 converts arachidonic acid into prostaglandins. The latter stimulate cell proliferation. The $G\alpha_{12}$ mutant also has the property of inducing the transcription of COX-2, which leads to the constitutive expression of COX-2 in cells engineered to express the mutant.

Contact of indicator cells with an inhibitor of COX-2 has the effect of inhibiting production of prostaglandins, and thus cell proliferation. At the same time, the prostaglandin precursor arachidonic acid will accumulate in the cell or culture medium due to the blockage of COX-2-mediated conversion of arachidonic acid to prostaglandin.

One such $G\alpha_{12}$ mutant is the protein $G\alpha_{12}Q229L$ ("$G\alpha_{12}QL$") described by Xu et al., supra. The starting material for the $G\alpha_2QL$ (also referred to herein as "Q0229L") mutant is the full-length murine wild-type $G\alpha_{12}$ cDNA disclosed by Strathman and Simon, *Proc. Natl. Acad. Sci. (USA)* 1991; 88:5582–5582 or GenBank accession record M63659. The mutant is generated by the method described by Xu et al., supra, utilizing site-directed mutagenesis of double-stranded DNA by overlap extension using PCR methodology. The mutagenic oligonucleotides have the following sequences, wherein the modified nucleotides are underlined: 5'-TGGGCGGCCTGAGGTCAC-3' (SEQ ID NO:1) and 5'-GTGACCTCAGGCCGCCCA-3' (SEQ ID NO:2).

Figure 1:
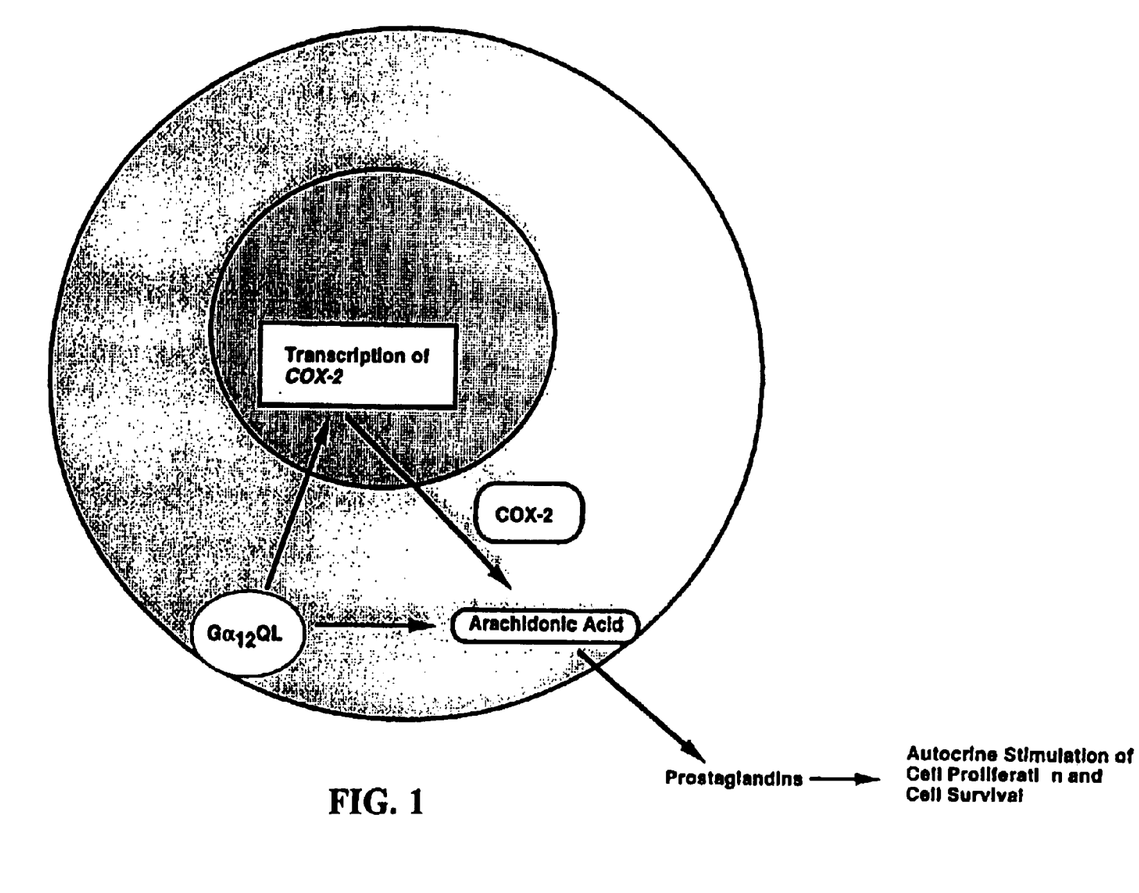
FIG. 1 is a schematic representation of the mechanism by which COX-2 plays a role in proliferation of cells expressing the GTPase-deficient $G\alpha_{12}QL$ mutant.

Cells engineered to express $G\alpha_{12}QL$ are driven to proliferation through an autocrine loop shown in FIG. 1. COX-2 inhibitors can arrest cell proliferation by disrupting this autocrine loop. Such an inhibitory effect can be easily quantified by monitoring the $G\alpha_2QL$-stimulated synthesis of DNA A putative COX-2 inhibitor can thus be easily and rapidly screened for COX-2 inhibitory activity.

Prior to the present invention, it was not known that the Q229L mutation induces COX-2 transcription in cells. It has been unexpectedly found that $G\alpha_{12}QL$-transformed cells constitutively express COX-2, thereby permitting their use as reagents for screening putative COX-2 inhibitors.

According to the invention, a host cell line capable of growth in culture, preferably a fibroblast line (e.g. NIH 3T3), is transfected with a construct which will drive $G\alpha_{12}QL$ DNA expression in the host cell line. The construct contains $G\alpha_{12}QL$ DNA and appropriate control elements. The construct may contain a non-inducible promoter, or an inducible promoter, e.g., an isopropyl-β-D-1-thiogalactopyranoside (IPTG)-inducible promoter. Methods for establishing cell lines that expresses $G\alpha_{12}QL$ under control of an IPTG promoter are described by Vara Prasad et al., *J. Biol. Chem.* 1995, 270:18655–18659, the entire disclosure of which is incorporated herein by reference.

Cells of the transfected cell line which produce arachidonic acid and COX-2 are then used as indicator cells for testing the COX-2 inhibitory activity of test substances. The test substance may comprise a pure chemical compound or mixture of chemical compounds. Typically, the test substance will be an essentially pure chemical compound which may be contained in a suitable carrier for administration to the indicator cell culture. An appropriate concentration of test substance is introduced into the cell culture. An appropriate concentration can be determined by trial and error, without undue experimentation. The concentration of test substance may range, for example, from about 0.1 to about 100 µM, more typically from about 1 to about 20 µM, most typically from about 1 to about 10 µM.

According to one embodiment of the invention, the level of proliferation of the indicator cells with and without the test substance present in the cell culture is then determined. The test substance is contacted with the indicator cells under conditions which favor the proliferation of those cells. Methods for culturing cells under conditions of proliferation are well-known to those skilled in the art. Typically, conditions favoring cell proliferation in culture comprise culturing the cells in the presence of a growth medium, e.g., a growth medium comprising a serum such as fetal bovine serum (FBS). Assays for determining the level of proliferation of cells in culture are well-known to those skilled in the art. In addition to determining actual cell number, several indirect methods for assessing cell proliferation are known to those skilled in the art.

According to one preferred embodiment of a proliferation assay, proliferation is assessed by monitoring DNA synthesis. Proliferating cells actively synthesize DNA to support mitosis. DNA synthesis may be conveniently monitored through the cell's uptake of detectably labeled DNA precursors. Such labeled precursors include, for example, chemically-labeled and radiolabeled precursors. One chemically labeled precursor is bromodeoxyuridine. Bromodeoxyuridine incorporation can be detected by bromodeoxyuridine-antibodies in an enzyme linked immunosorbent assay using fixed microcultures (Muir et al., *Analytical Biochemistry* 1990; 185:377–382). The preferred radiolabeled precursor is tritium-labeled thymidine ($^3$H-thymidine). Other chemically labeled and radiolabeled DNA precursors suitable for use in cell proliferation assays are known to those skilled in the art. The capacity of the test substance to inhibit cell proliferation is a measure of the potency of the substance as an inhibitor of COX-2 activity.

According to another embodiment of the invention, the level of one or more prostaglandins produced by the indicator cells, with and without the test substance present in the cell culture, be can determined. Such prostaglandins may include for example $PGE_2$, $PGF_{2\alpha}$, $PGD_2$, their stabilized chemical derivatives and the like. In samples were the chemical environment promotes the rapid turnover of prostaglandins such prostaglandins may be converted to stable derivatives prior to detection. Such stabilized derivatives include for example bicyclo prostaglandin E2, 8-isoprostane, and prostaglandin D2 methoxime which correspond to $PGE_2$, $PGF_2$, and $PGD_2$. A decrease in production of prostaglandins by the indicator cells in the presence of the test substances indicates that the test substance has COX-2 inhibitory activity. Assays for determining the level of prostaglandins produced by cells in culture are well-known to those skilled in the art. Such methods include, for example, chromatography-based techniques, receptor based assays or immunoassays for the prostaglandin(s) of interest.

Receptor based prostaglandins assays may be based on the methods of Hanasaki et al. or Balapure et al. for example. Hanasaki et al., J. Biol. Chem. 1990; 265:4871–4875 and Balapure et al., Biochem. Pharmacol. 1989; 38:2375–2381. Prostaglandin production may be measured by the various methods in the media surrounding cells, in the cells themselves, or in a component of the cells. Components of the cells include for example organelles, membranes, proteins, cell lysates, cell pellets, cell supernatants and the like.

For example, prostaglandin production in radiolabeled cells may be assayed by a thin layer chromatography (TLC) as follows. Radiolabeled prostaglandins are extracted from cells, their components, or the surrounding media with an appropriate solvent such as ethyl acetate. The solvent-extracted radiolabeled prostaglandins are then spotted on a TLC plate and developed under suitable conditions in an appropriate mobile phase. Radiolabeled prostaglandins may be detected by any suitable means such as phosporimaging, fluorography, scintillation counting, autoradiography and the like. Alternatives to TLC chromatography include any chromatography technique capable of discerning the relative amounts of prostaglandins produced by unlabeled or radiolabeled cells.

According to one preferred embodiment of the invention, prostaglandin production by the indicator cells is measured by a competitive immunoassay. In such an assay, a primary antibody specific to one or more prostaglandins is incubated with a sample to be analyzed followed by incubation of the sample with an immobilized secondary antibody specific to the primary antibody. A labeled prostaglandin is then incubated with the sample, and the labeled prostaglandin is allowed to compete with non-conjugated prostaglandins in the sample for prostaglandin binding sites on the primary antibody. The competing labeled prostaglandin may be labeled by any suitable means including radiolabeling, conjugation with a peroxidase or other easily detected polypeptide, chromophore labeling, or fluorophore labeling. Techniques for labeling prostaglandins are well known to those skilled in the art. The level of competing, labeled prostaglandin bound after washing is inversely related to the amount of prostaglandin present in the sample analyzed. (Shaw and Ramwell, *Methods of Biochem. Analysis* 1969; 17:325–371; Green et al., *Advances in Prostaglandin and Thromboxane Res.* 1978; 5:15–38; Powell, *Prostaglandins* 1980; 20:947–957; Kelly et al., *Prostaglandins, Leukotrienes and Essential Fatty Acids* 1989; 37:187–191; Granstrom and Kindhal, Advances in Prostaglandin and Thromboxane Res. 1980; 5:119–210; Morris et al., *Prostaglandins* 1981; 21:771–778; Granstrom and Samuelsson, *Advances in Prostaglandin and Thromboxane Res.* 1978; 5:1–13). A competitive prostaglandin assay permits rapid, high throughput screening for COX-2 inhibitors using the indicator cells of the invention.

As an alternative to measuring prostaglandin production by the indicator cells, the level of arachidonic acid provided by the indicator cells is determined, with and without the test substance present in the cell culture. By a "level" of arachidonic acid which is "provided" by the indicator cells, is meant the relative amount or concentration of arachidonic acid in the cells or component thereof, or in the culture medium. Arachidonic acid is readily converted to prostaglandins in the presence of functional COX-2. An increase in the level of arachidonic acid by the indicator cells in the presence of the test substance indicates that the test substance has COX-2 inhibitory activity. Assays for determining the level of arachidonic acid produced by cells in culture are well-known to those skilled in the art. Arachidonic acid production may be measured in the media surrounding cells, in the cells themselves or in components of the cells. According to one preferred embodiment of the invention, arachidonic acid release is measured by labeling indicator cells with tritiated arachidonic acid ([$^3$H]-arachidonic acid), washing cells to remove free radiolabeled arachidonic acid, treating the cells with the test substances and after a time measuring by scintillation counting the radiolabeled arachidonic acid present in the media surrounding the cells. (Xu at al., supra). In the absence of functioning COX-2 the radiolabelled arachadonic acid taken up by the cells is not converted to prostaglandin, but rather is released to the surrounding media.

The inhibitory compounds identified using the invention may be administered to individuals (animals, most particularly mammals including humans) afflicted with any disorder characterized by undesirable prostaglandin production resulting from cyclooxygenase activity, particularly COX-2 activity ("cyclooxygenase-mediated disorder"). In particular, COX-2 inhibitory compounds of the type identified using the invention are believed useful in treating inflamation and inflamation-related disorders, by administering to a subject having or susceptible to such inflamation or inflamation-related disorder and effective amount of an inhibitory compound. Inflamation is associated with a variety of disease conditions. For a list of such disease conditions treatable by cyclooxygenase inhibitors, and COX-2 inhibitors in particular, see U.S. Pat. Nos. 5,604,253 and 5,908,852, the entire disclosures of which are incorporated herein by reference. Such conditions include, for example, arthritis, including but not limited to rheumatoid arthritis, spondyloarthropathies, gouty arthritis, osteoarthritis, systemic lupus erythematosus and juvenile arthritis. Such conditions further include rheumatic fever, symptoms associated with influenza or other viral infections, common cold, low back and neck pain, dysmenorrhea, headache, toothache, sprains and strains, myositis, neuralgia, synovitis, gout and ankylosing spondylitis, bursitis, and following surgical and dental procedures. COX-2 inhibitory compounds are also believed useful as analgesics for treating or alleviating all forms of pain. The compounds are believed useful in the treatment of other disorders including asthma, bronchitis, tendinitis, bursitis; skin related conditions such as psoriasis, eczema, burns and dermatitis; gastrointestinal conditions such as inflammatory bowel disease, Crohn's disease, gastritis, irritable bowel syndrome and ulcerative colitis and for the prevention of colorectal cancer; the treatment of inflamation in such diseases as vascular diseases, migraine headaches, periarteritis nodosa, thyroiditis, aplastic anemia, Hodgkin's disease, sclerodoma, type I diabetes, myasthenia gravis, sarcoidosis, nephrotic syndrome, Behcet's syndrome, polymyositis, gingivitis, hypersensitivity, conjunctivitis, swelling occurring after injury, myocardial ischemia, and the like. The COX-2 inhibitory compounds identified using the invention are also believed useful as antipyretics for the treatment of fever.

In addition, COX-2 inhibitors of the type identified using the invention may inhibit cellular neoplastic transformations and metastatic tumor growth and hence can be used in the treatment of cancer. The term "neoplasia" includes neoplasias that produce prostaglandins or express a cyclooxygenase, including both benign and cancerous tumors, growths and polyps. Neoplasias believed treatable with cyclooxygenase inhibitors are discussed in U.S. Pat. No. 5,972,986, the entire disclosure of which is incorporated herein by reference. The COX-2 inhibitors identified using the invention may be used to inhibit the growth of an established neoplasm, i.e., to induce regression, or to prevent or delay the onset of the neoplasm.

According to U.S. Pat. No. 5,972,986, neoplasias that produce prostaglandins, and which are therefore believed treatable with compounds of the type identified using the invention, include brain cancer, bone cancer, epithelial cell-derived neoplasia (epithelial carcinoma) such as basal cell carcinoma, adenocarcinoma, gastrointestinal cancer such as lip cancer, mouth cancer, esophageal cancer, small bowel cancer and stomach cancer, colon cancer, liver cancer, bladder cancer, pancreas cancer, ovary cancer, cervical cancer, lung cancer, breast cancer and skin cancer, such as squamous cell and basal cell cancers, prostate cancer, renal cell carcinoma, and other known cancers that effect epithelial cells throughout the body.

The COX-2 inhibitory compounds identified by using the invention may also be useful in the treatment of angiogenesis-mediated disorders. Angiogenesis-mediated disorders which may be treatable with cyclooxygenase inhibitors are discussed in U.S. Pat. No. 6,025,353, the entire disclosure of which is incorporated herein by reference. According to U.S. Pat. No. 6,025,353, such disorders include, for example, metastasis, corneal graft rejection, ocular neovascularization, retinal neovascularization, diabetic retinopathy, retrolental fibroplasia, neovascular glaucoma, gastric ulcer, infantile hemaginomas, angiofibroma of the nasopharynx, avascular necrosis of bone, and endometriosis.

The practice of the invention is illustrated by the following non-limiting examples.

EXAMPLE 1

Establishing $G\alpha_{12}QL$ Cell Line

A. Transfection of NIH3T3 Cells with $G\alpha_{12}QL$ Vector (i) Preparation of $G\alpha_{12}QL$-NIH3T3

The vector $G\alpha_{12}QL$-pcDNA3 was prepared by ligating the EcoRI-XbaI (1.8 kb) fragment from pcDNA1-$\alpha_{12}$Q229L into the EcoRI-XbaI site of the pcDNA3 vector (Invitrogen, Carlsbad, Calif.). Actively proliferating NIH 3T3 cells (1.5× $10^6$ cells/100 mm dish) grown in Dulbecco's modified Eagle's medium (DMEM) containing 10% FBS were transfected with 100 ng of the vector by the calcium precipitation method. The procedures for transfection and transformation of NIH 3T3 cells have been previously described (Vara Prasad et al., *Oncogene* 1994, 9:2425–2429, and Shore & Reddy, *Oncogene* 1989, 4:1411–1423, the entire disclosures of which are incorporated herein by reference.) Individual transformed foci were isolated and expanded for further analysis by Northern and Western analyses for $G\alpha_{12}QL$ expression as well as anchorage-independent growth in soft-agar according to previously published procedures (Vara Prasad et al., 1994, supra).

(ii) Preparation of IPTG-inducible $G\alpha_{12}QL$-NIH3T3

An NIH3T3 cell line that expresses $G\alpha_{12}QL$ under an IPTG-inducible promoter ($G\alpha_{12}QL$-pOPRSVI-NIH3T3) was established as previously described (Vera Prasad et al, 1995, supra), as follows. Blunt-ended 1.8 kb HindIII-XbaI fragment of $\alpha_{12}$Q229L excised from the $G\alpha_2QL$-pcDNA3 vector was ligated into the blunted NotI site of the pOPRSVI plasmid following published procedures (Sambrook et al. (1989) *Molecular Cloning: A Laboratory Manual* 2d Ed., Cold Spring Harbor Laboratory Press, Cold Spring Harbor, N.Y.). NIH3T3 cell lines expressing inducible $\alpha_2$Q229L were established using the LacSwitch expression vectors (Stratagene). Briefly, NIH3T3 cell were cotransfected with p3'SS plasmid vector expressing the Lac repressor and pOPRSVI-$\alpha_2$Q229L vector by electroporation, as described by Vera Prasad et al., 1995.

B. Preparation of COX-2 DNA

Murine COX-2 DNA was cloned using RT-PCR methods from the RNA prepared from NIH 3T3 cells pretreated (6 hrs) with 100 nM PMA using the following primers: 5'CTCTGCGATGCTCTTCCGAG-3' (SEQ ID NO:3) and 5'-GACTTTTACAGCTCAGTTGAACG-3' (SEQ ID NO:4). The amplified 1827 bp PCR-product was sequenced and the comparison with the published sequences (Kujubu et al., *J. Biol. Chem.* 1991, 266, 12866–12872) confirmed the identity of COX-2 cDNA. The COX-2 PCR-product was purified and cloned into pT7Blue TA vector (Novagen, Madison, Wis.). The clone was used as a source of probes for Northern blot analysis.

C. Confirmation of COX-2 Expression in IPTG-inducible $G\alpha_{12}QL$-NIH3T3 Cells 1. Northern Blotting Expression of $G\alpha_{12}QL$ was induced in the IPTG-inducible $G\alpha_{12}QL$-NIH3T3 cells and control cells by the addition of 1 mM IPTG. At 0, 0.5, 1, 3, and 6 hours after the addition of IPTG, total RNA was prepared from the cells following the published procedures of Dhanasekaran et al., *J. Biol. Chem.* 1993, 269:11802–11806, the entire disclosure of which is incorporated herein by reference. Twenty µg of the RNA (for each time point) was resolved in a denaturing 1% agarose and 2.2 M formaldehyde gel. The RNA was blotted onto a zeta probe-GT membrane (Bio-Rad, Calif.) and cross-linked to the membrane by UV light. The Hind III-Xba I fragment (1.2 kbp) of $G\alpha_{12}QL$ DNA excised from $G\alpha_{12}QL$ and the Xba I-Bam HI fragment (1.8 kbp) of COX-2 from the COX-2pT7Blue vector were used as probes in Northern blot analyses. The RNA was also probed for GAPDH expression.

Figure 2A:
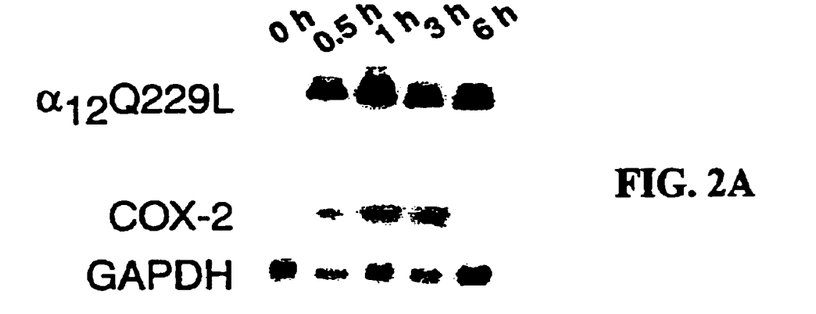
FIG. 2A is a Northern blot of analysis of RNA from IPTG-inducible $G\alpha_{12}QL$-NIH3T3 cells stimulated with 1 mM IPTG for 0, 0.5, 1, 3 and 6 hours. Cells were probed with DNA encoding $G\alpha_{12}QL$, COX-2 or GAPDH.
Figure 2B:
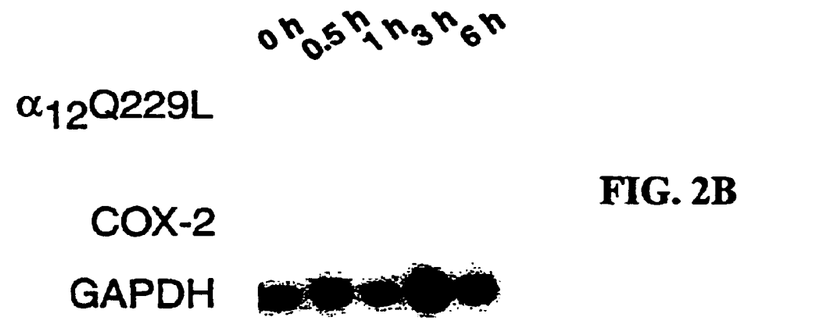
FIG. 2B is similar to FIG. 2A, except that the analysis was carried out on control cells. The control cells were NIH3T3 cells transfected with vector lacking the $G\alpha_{12}QL$ insert.

The results of the Northern blot analysis are shown in FIGS. 2A ($G\alpha_{12}QL$-3NIH3T3) and 2B (control cells). The control cells were NIH3T3 cells transfected with "empty" pOPRSVI vector lacking the $G\alpha_{12}QL$ insert. COX-2 transcription was induced only in $G\alpha_{12}QL$-NIH3T3 cells.

2. Western Blotting

The constitutive expression of COX-2 protein was demonstrated by Western blot analysis. Cell lysates for Western blot analysis were prepared from control NIH3T3, NIH3T3 expressing wild type $G\alpha_{12}$ ($G\alpha_{12}$WT-NIH3T3) and $G\alpha_{12}QL$-NIH3T3 cells. The cells grown in 100 mm dishes, washed twice in phosphate-buffered saline (PBS) and lysed with 0.5 ml of RIPA buffer (10 mM $NaPO_4$ pH 7,0, 150 mM NaCl, 2 mM EDTA, 1% sodium deoxycholate, 1% NP40, 0.1% SDS, 50 mM NaF, 200 mM $Na_3VO_4$, 0.1% β-mercaptoethanol, 1 mM phenylmethanesulfonyl-fluoride (PMSF), 4 µg/ml aprotinin, and 2 µg/ml leupeptin). The soluble proteins were cleared by centrifugation at 15,000 g for 10 minutes at 4° C. The lysate (50 µg) was resolved by SDS-PAGE and electroblotted onto polyvinylidene fluoride (PVDF) membranes (Millipore, Bedford, Mass.) in 10 mM 3-cyclohexylamino-1-propane sulfonic acid (CAPS) buffer containing 10% methanol using a Mini-Protean apparatus (Bio-Rad, CA). The resolved lysates were probed with specific antibodies raised against the C-terminus of COX-2 (Oxford Biomedical Research, MI).

Figure 3:
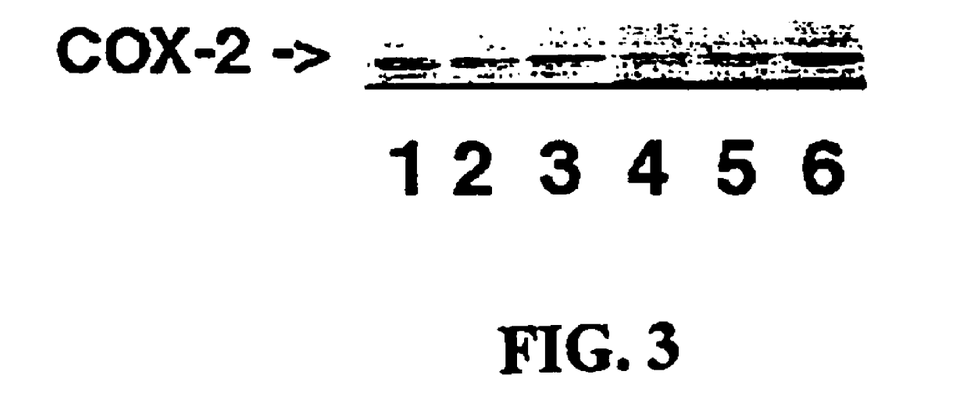
FIG. 3 is Western blot analysis of cell lysates probed for COX-2 expression. The lysates were prepared from $G\alpha_2QL$-NIH3T3 cells (lanes 3 and 6), control NIH3T3 cells (lanes 1 and 4) and $G\alpha_{12}$WT-NIH3T3 cells expressing wild type $G\alpha_{12}$ (lanes 2 and 5).

The results are shown in FIG. 3. COX-2 is constitutively expressed in $G\alpha_{12}QL$-NIH3T3 cells (lanes 3 and 6) but not in control NIH3T3 cells (lanes 1 and 4) or $G\alpha_{12}$WT-NIH3T3 cells (lanes 2 and 5).

EXAMPLE 2

Inhibition of $G\alpha_{12}QL$-NIH3T3 Cell Proliferation by COX-2 Inhibitor

Figure 4:
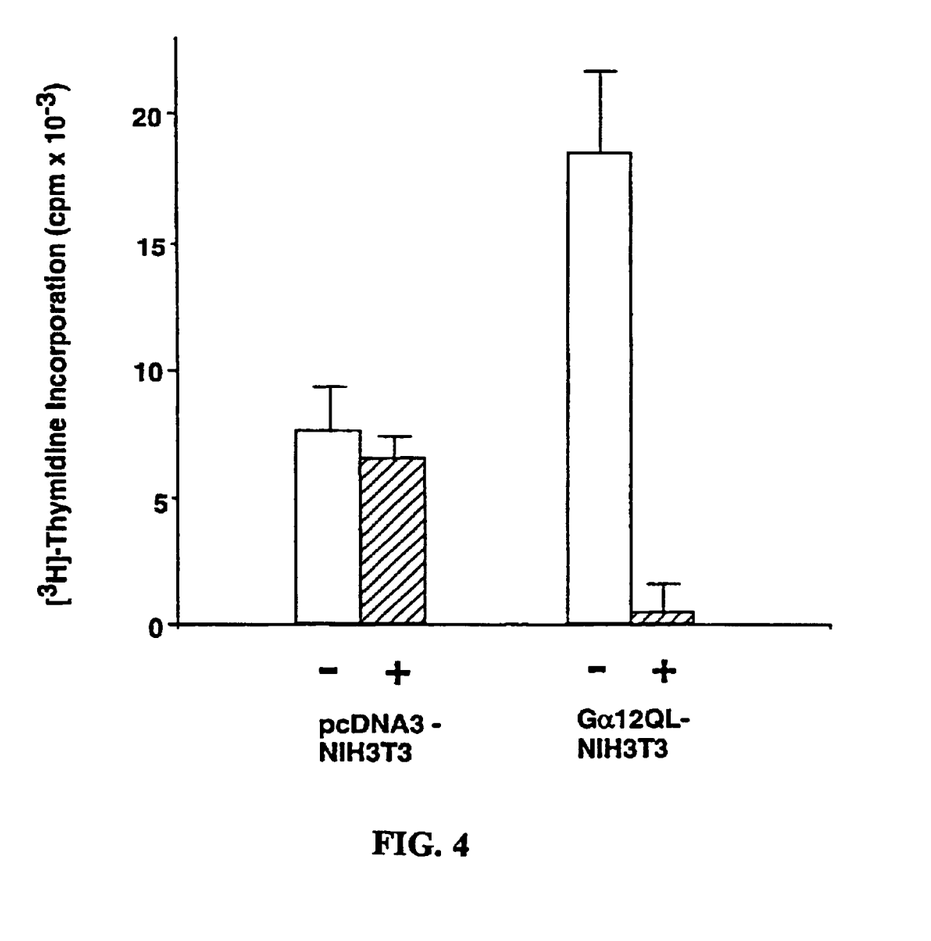
FIG. 4 is a graph of [$^3$H]-thymidine incorporation as an index of DNA synthesis in NIH3T3 cells transfected with $G\alpha_{12}QL$ DNA ($G\alpha_{12}QL$-NIH3T3) versus control NIH3T3 cells transfected with vector alone (pcDNA3-NIH3T3). Groups treated with a COX-2 inhibitor at 10 µM are a labeled with a "+" symbol, while groups not treated with a COX-2 inhibitor are labeled with a "−" symbol. Values represent the mean ±S.E. from a triplicate determination.

Inhibition of $G\alpha_{12}QL$-NIH3T3 cell proliferation by a COX-2 inhibitor was determined by monitoring DNA synthesis. [³H]-Thymidine incorporation was used as an index of DNA-synthesis. Control cells (expressing pcDNA3 vector) and Gα₂QL-transformed NIH 3T3 cells were plated at 5×10⁴ cells per well in a 24-well plate and grown for 24 hours at 37° C. in DMEM containing 5% FBS. The cells were washed and made quiescent by placing them in DMEM (+0.2% BSA) without serum for an additional 24 hours. Cell growth was reinitiated by the addition of 10% FBS with or without an experimental COX-2 inhibitor (10 μM). Twelve hours later 1 μCi of thymidine (20 Ci/nmol) was added to each well and incubated for an additional 4 hours. The cells were washed in PBS and solubilized in 0.1% SDS. DNA was precipitated with 10% chilled TCA and the precipitate was collected on GFC filters. The counts in the precipitate were determined by scintillation counting. The results are shown in FIG. 4. The values represent the mean ± the standard error for triplicate determinations.

The addition of 10 μM COX-2 inhibitor did not have any effect on control cells. In contrast, the COX-2 inhibitor specifically inhibited DNA synthesis in Gα₁₂QL-NIH3T3 cells as shown in FIG. 4. These results indicated that the COX-2-inhibitor did not affect normal cells but arrested cell growth in transformed cells dependent on the COX-2 pathway for cell growth and survival. Since Gα₁₂QL-NIH3T3 cells exhibit such a phenotype, the bioassay system based on Gα₁₂QL-NIH3T3 cells may be effectively used to screen putative COX-2 inhibitors.

EXAMPLE 3

Determination of Prostaglandin Levels as an Assay for COX-2 Activity

Figure 5:
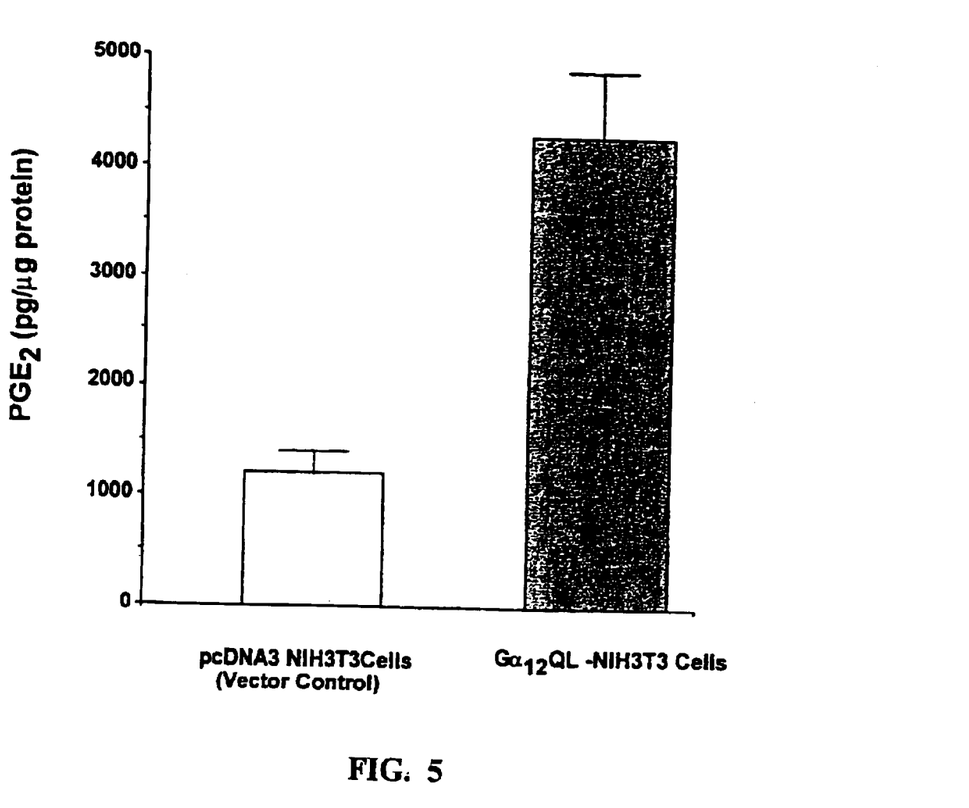
FIG. 5 is a graph of prostaglandin release from NIH3T3 cells as a function of stable transfection with $G\alpha_{12}QL$ expression vectors and pcDNA3. Values represent the mean ±S.E. from a triplicate determination.

Activation of prostaglandin release by NIH3T3 cells in response to Gα₁₂QL expression was determined by monitoring prostaglandin production. Prostaglandin PGE₂ was used as an index of COX-2 mediated prostaglandin production. Control NIH3T3 cells stably transfected with pcDNA3 vector and Gα₁₂QL-transformed NIH3T3 cells were plated at 3×10⁶ cells per 100 mm dish and grown overnight at 37° C. in DMEM containing 5% FBS. The cells were washed and made quiescent by placing them in DMEM (+0.2% BSA) without serum for an additional 24 hours. Cell growth was reinitiated by the addition of 10% FBS. Six hours later the cells were pelleted by centrifugation. The cell pellet was lysed and total cellular PGE₂ production was measured using a competitive enzyme immunoassay (Prostaglandin E₂ EIA (enzymeimmunoassay) Kit, Cayman Chemical Co., Ann Arbor, Mich., USA) as per the manufacturer's protocol. The results are shown in FIG. 5. The values represent the mean ± the standard error for triplicate determinations.

Stable expression of Gα₁₂QL dramatically activated prostaglandin PGE₂ production in the indicator cells in contrast to control NIH3T3 cells stably transfected with pcDNA3 as shown in FIG. 5. Activation or inhibition of COX-2 activity in Gα₁₂QL transfected indicator cells can be assessed by determining the levels of prostaglandins produced by such indicator cells. The assay may be used to screen candidate compounds for inhibition of COX-2 activity.

EXAMPLE 4

Determination of Arachidonic Acid Levels as an Assay for COX-2 Activity

Figure 6A:
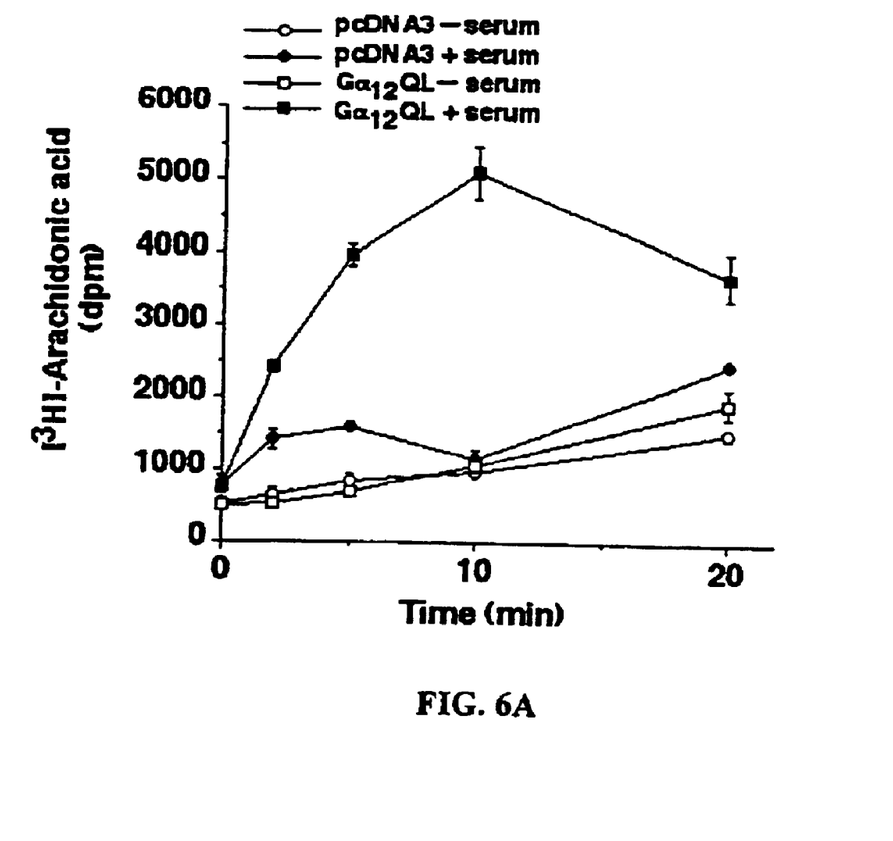
FIG. 6A is a graph of [$^3$H]-arachidonic acid release from $G\alpha_{12}QL$ expression vector or pcDNA3 transfected NIH3T3 cells. Quiescent, stably transfected cells were stimulated with serum and [$^3$H]-arachidonic acid release was followed as a function of time. Values represent the mean ±S.E. from a triplicate determination.

Arachidonic acid release levels can be used as an index of COX-2 activity. Control NIH3T3 cells stably transfected with pcDNA3 vector and Gα₁₂QL-transformed NIH3T3 cells were plated at 2×10⁴ cells per well in a 24-well plate and grown for 24 hours at 37° C. in DMEM containing 5% FBS. Cells were labeled and made quiescent by incubation for 24 hrs with 0.5 ml serum free DMEM containing 10 mM HEPES (ph 7.4), 0.2% BSA and 0.5 μCi [³H]-arachidonic acid per well. Cells were then washed three times with PBS to remove free [³H]-arachidonic acid. Cell growth was reinitiated by the addition of FBS to a final concentration of 5% [³H]-Arachidonic acid release into the surrounding media was measured at 0, 2, 5, 10, and 20 min after serum stimulation by scintillation counting as per the method of Xu et al., supra. Prior to scintillation counting cell debris in the media was removed by centrifugation at 2000 g. [³H]-arachidonic acid release by non-serum stimulated cells into the surrounding media was measured at 0, 2, 5, 10, and 20 min by scintillation counting. The results are shown in FIG. 6A. The values represent the mean ± the standard error for triplicate determinations.

Serum stimulation of Gα₂QL transfected cells dramatically increased arachidonic acid release in contrast to non-serum stimulated indicator cells as shown in FIG. 6A. Arachidonic acid release by control NIH3T3 cells stably transfected with pcDNA3 was unaffected by serum stimulation as shown in FIG. 6A. Activation or inhibition of COX-2 activity in Gα₂QL transfected indicator cells can be assessed by determining the levels of arachidonic acid produced by such indicator cells. Inhibition of COX-2 will presumably increase arachidonic acid levels as such inhibition will prevent conversion of arachidonic acid into the various prostaglandins.

Figure 6B:
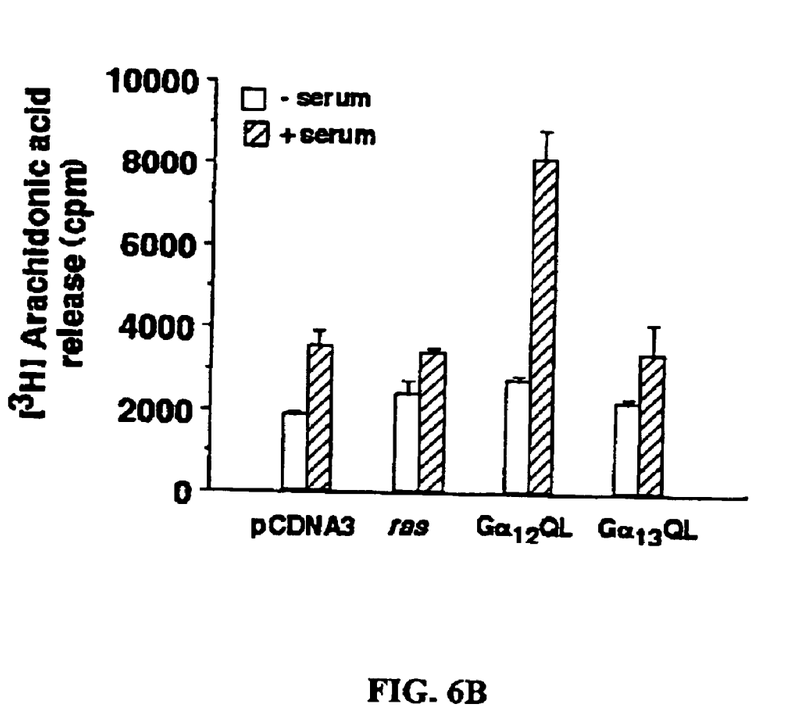
FIG. 6B is a graph of [$^3$H]-arachidonic acid release from pcDNA3, ras, $G\alpha_{12}QL$, and $G\alpha_{13}QL$ expression vector stably transfected NIH3T3 cells. Quiescent, transfected cells were stimulated with serum and [$^3$H]-arachidonic add release was measured after 10 minutes. Values represent the mean ±S.E. from a quadruplicate determination.

Arachidonic acid release levels were also used as an index of COX-2 activity in NIH3T3 cells stably transfected with pcDNA3, ras, Gα₁₂QL, and Gα₁₃QL expression vectors as shown in FIG. 6B. Cells were plated, labeled with [³H]-arachidonic acid, and [3H]-arachidonic acid release was measured using the methodologies described above. [³H]-arachidonic acid release was measured by scintillation counting 10 min after reinitiation of cell growth by addition of 5% FBS. The results are shown in FIG. 6B. The values represent the mean ± the standard error for quadruplicate determinations.

As FIG. 6B shows, serum stimulation of Gα₂QL transfected indicator cells dramatically increased arachidonic acid release relative to cells stably transfected with pcDNA3, ras, or Gα₁₃QL expression vectors as shown in FIG. 6A. These results demonstrate the apparent specificity with which Gα₁₂QL expression stimulates the COX-2 pathway. Activation or inhibition of COX-2 activity in Gα₁₂QL transfected indicator cells can be assessed by determining the levels of arachidonic acid produced by such indicator cells. The assay may be used to screen candidate compounds for inhibition of COX-2 activity.

All references cited with respect to synthetic, preparative and analytical procedures are incorporated herein by reference. All sequence records identified by GenBank accession numbers are incorporated herein by reference.

The present invention may be embodied in other specific forms without departing from the spirit or essential attributes thereof and, accordingly, reference should be made to the appended claims, rather than to the foregoing specification, as indication the scope of the invention.

What is claimed is:

1. A method for screening a test substance for COX-2 inhibitory activity comprising:
   (a) contacting the test substance with indicator cells which express a GTPase-deficient mutant form of the α-subunit of protein G12, wherein the G12 protein α-subunit mutant comprises the Q229L mutation, which mutant α-subunit has the capacity to induce the production of arachidonic acid in the indicator cells, and induces production of COX-2 in the indicator cells; and
   (b) determining the level of one or more prostaglandins produced by the indicator cells in the presence and absence of the test substance, a decrease in production of said prostaglandin by the indicator cells in the presence of the test substance indicating that the test substance has COX-2 inhibitory activity.

2. A method according to claim 1 wherein the prostaglandin level is assayed in the media surrounding the indicator cells, in the indicator cells or in a component of the indicator cells.

3. A method according to claim 1 wherein the prostaglandin level is assayed by a prostaglandin immunoassay.

4. A method according to claim 1 wherein the prostaglandin immunoassay comprises a competitive immunoassay.

* * * * *

UNITED STATES PATENT AND TRADEMARK OFFICE
CERTIFICATE OF CORRECTION

| | | |
|---|---|---|
| PATENT NO. | : 6,933,128 B1 | Page 1 of 1 |
| APPLICATION NO. | : 10/018581 | |
| DATED | : August 23, 2005 | |
| INVENTOR(S) | : E. Premkumar Reddy, M. V. Ramana Reddy and Natarajan Dhanasekaran | |

It is certified that error appears in the above-identified patent and that said Letters Patent is hereby corrected as shown below:

Column 1, lines 16-18, cancel the text and insert the following:

--This invention was made with government support under grant GM49897 awarded by the National Institutes of Health. The government has certain rights in the invention.--

Signed and Sealed this

Fourth Day of October, 2011

David J. Kappos
*Director of the United States Patent and Trademark Office*